(12) United States Patent
Chao et al.

(10) Patent No.: US 7,249,886 B1
(45) Date of Patent: Jul. 31, 2007

(54) METHOD AND APPARATUS FOR MEASURING EFFECTIVE FOCAL SPOT PARAMETERS OF AN X-RAY SOURCE

(75) Inventors: Edward Henry Chao, Oconomowoc, WI (US); Bruce Matthew Dunham, Mequon, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/443,239

(22) Filed: May 30, 2006

(51) Int. Cl.
*G01D 18/00* (2006.01)
(52) U.S. Cl. .................................... 378/207; 378/113
(58) Field of Classification Search ............... 378/207, 378/117–118, 16, 205, 113, 93, 4
See application file for complete search history.

(56) References Cited

U.S. PATENT DOCUMENTS

| | | | |
|---|---|---|---|
| 4,442,539 A | 4/1984 | Aichinger et al. | |
| 5,606,591 A | 2/1997 | Montel et al. | |
| 5,872,830 A | 2/1999 | Herrndorf | |
| 6,233,348 B1 | 5/2001 | Fujii et al. | |
| 6,327,331 B1 * | 12/2001 | Toth et al. | .......... 378/20 |
| 2002/0159566 A1 * | 10/2002 | Popescu | .......... 378/113 |

OTHER PUBLICATIONS

Everson, Gray "Focal-Spot Measurement: Comparison of slit, Pinhole, and Star Resolution Pattern Techniques" Rad. 165, 261 (1987).

* cited by examiner

*Primary Examiner*—Hoon Song
(74) *Attorney, Agent, or Firm*—Pete Vogel; Dean D Small; Small Patent Law Group

(57) ABSTRACT

A method for measuring focal spot shape of a radiation beam from a radiation source includes collimating the radiation beam using a collimator having a well-defined edge, measuring an intensity profile of the collimated radiation beam, determining a function of the measured intensity profile, and determining a metric of the of the focal spot using the determined function of the measured intensity profile.

19 Claims, 5 Drawing Sheets

METHOD AND APPARATUS FOR MEASURING EFFECTIVE FOCAL SPOT PARAMETERS OF AN X-RAY SOURCE

BACKGROUND OF THE INVENTION

This invention relates generally to x-ray source measurement methods and apparatus, and more particularly to methods and apparatus for measuring a focal spot profile of an X-ray source.

The X-ray source focal spot is an important physical parameter of a CT imaging system, x-ray imaging system, mammography system, radiation therapy system, or x-ray inspection system that influences the image resolution, slice sensitivity profile, dose profile, and many other image quality characteristics. The X-ray source is regularly replaced in imaging systems installed in a clinical setting, thus, it would be useful to measure the focal spot size and shape when the X-ray source is installed on the imaging system.

Additionally, the size and shape of the focal spot can vary over time, and changes in the focal spot size can be an indication of imminent tube failure. The ability to measure the focal spot size directly on the imaging system could therefore be used as a predictor of tube failure, enabling maintenance to be scheduled to minimize customer impact.

Additionally, X-ray sources may eventually have the capability to adjust their focal spot sizes in order to improve image quality or X-ray source reliability. However, to take advantage of this capability, focal spot size must be measured directly on the imaging system, without any additional equipment.

At least some methods for measuring focal spot size and shape are known, such as the pin-hole method (point spread function) or the slit method (line spread function). However, these methods require additional hardware (such as a pin-hole or a slit) not generally available on imaging systems.

BRIEF DESCRIPTION OF THE INVENTION

Accordingly, in one aspect, some configurations of the present invention provide a method for measuring focal spot shape of a radiation beam from a radiation source. The method includes collimating the radiation beam using a collimator having a well-defined edge, measuring an intensity profile of the collimated radiation beam, determining a function of the measured intensity profile, and determining a metric of the of the focal spot using the determined function of the measured intensity profile.

In another aspect, some configurations of the present invention provide an apparatus for measuring focal spot shape of a radiation beam. The apparatus includes a detector array sensitive to radiation, a radiation source configured to project a radiation beam at the detector array, a collimator having a well-defined edge and configured to collimate the radiation beam, and a processor configured to determine a function of a measured intensity profile. The apparatus is configured to measure an intensity profile of the collimated radiation beam, determine a function of the measured intensity profile, and determine a metric of the focal spot using the determined function of the measured intensity profile.

The advantage of using an edge spread function for measuring focal spot size is the availability of sharp edges in an imaging system X-ray beam path, such as an X-ray collimator. Other radiation devices such as a conventional X-ray diagnostic or a radiation therapy treatment device have similar well-defined edges in the radiation beam path.

The ability to determine a metric of a focal spot size/shape quickly and conveniently on a clinical imaging device could be used as a diagnostic for potential failure of the tube, or it could be used as a feedback for controlling the focal spot size dynamically to improve image quality.

Also, sharp edges in a CT imaging system X-ray beam path, such as an X-ray collimator, can be advantageously used with an edge spread function for measuring focal spot size. Other radiation devices such as a conventional X-ray diagnostic or a radiation therapy treatment device have similar well-defined edges in the radiation beam path, and thus can also use an edge spread function.

DETAILED DESCRIPTION OF THE INVENTION

Figure 1:
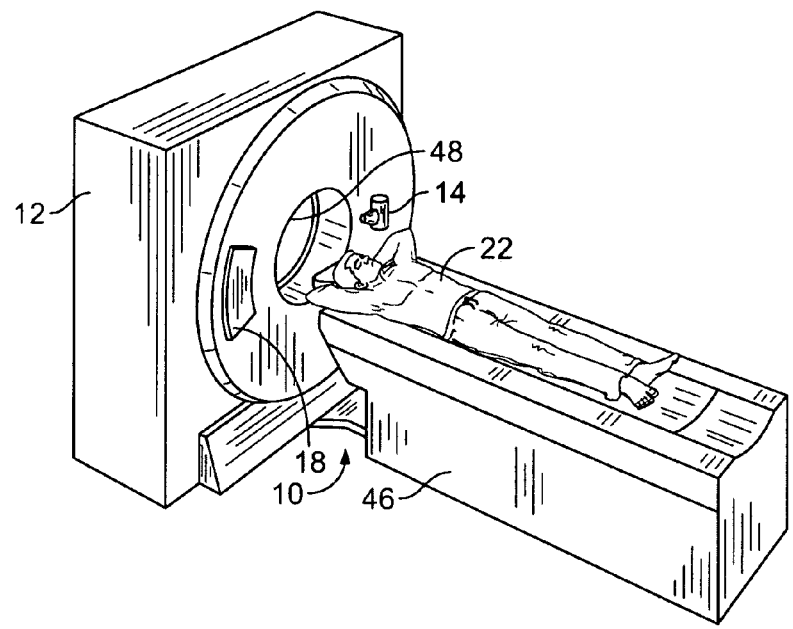
FIG. 1 is a drawing of a configuration of a computed tomographic (CT) imaging system, which is used as an example of one of the various types of imaging system configurations of the present invention.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered back projection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image. Also as used herein, the "shape" of an x-ray beam includes one or more metrics, which metric or metrics may consist of or include the size of the beam.

Figure 2:
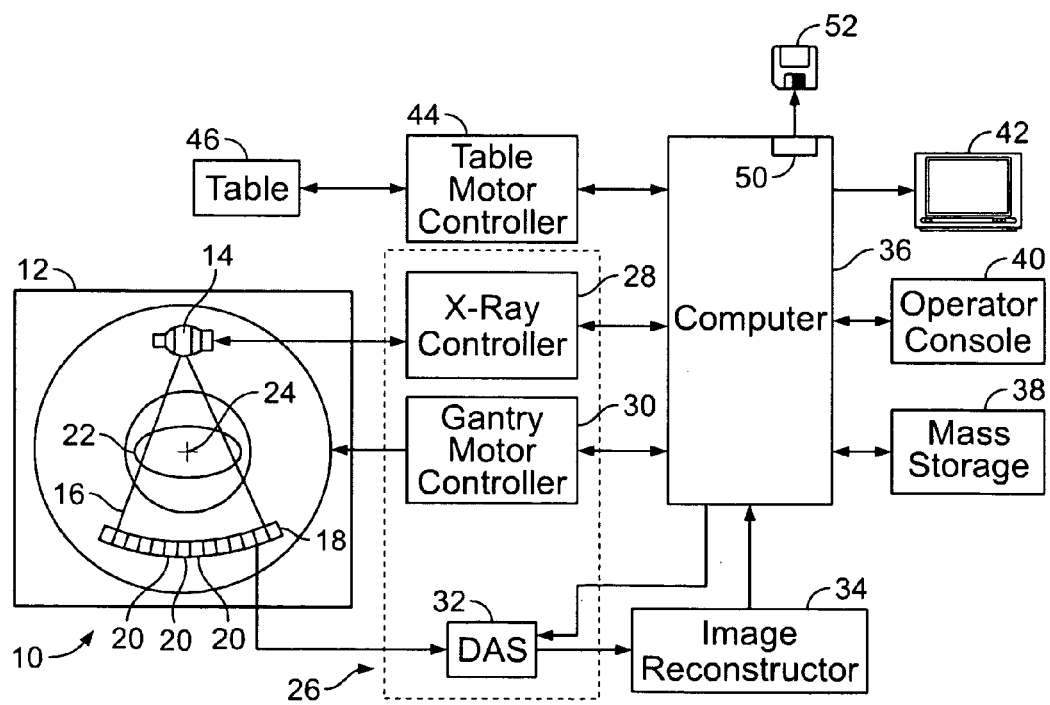
FIG. 2 is a schematic block diagram of the CT imaging system represented in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source or tube 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can comprise specialized hardware and/or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. For example, such imaging modalities include other types of x-ray imaging systems, mammography systems, radiation therapy systems, or x-ray inspection systems. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
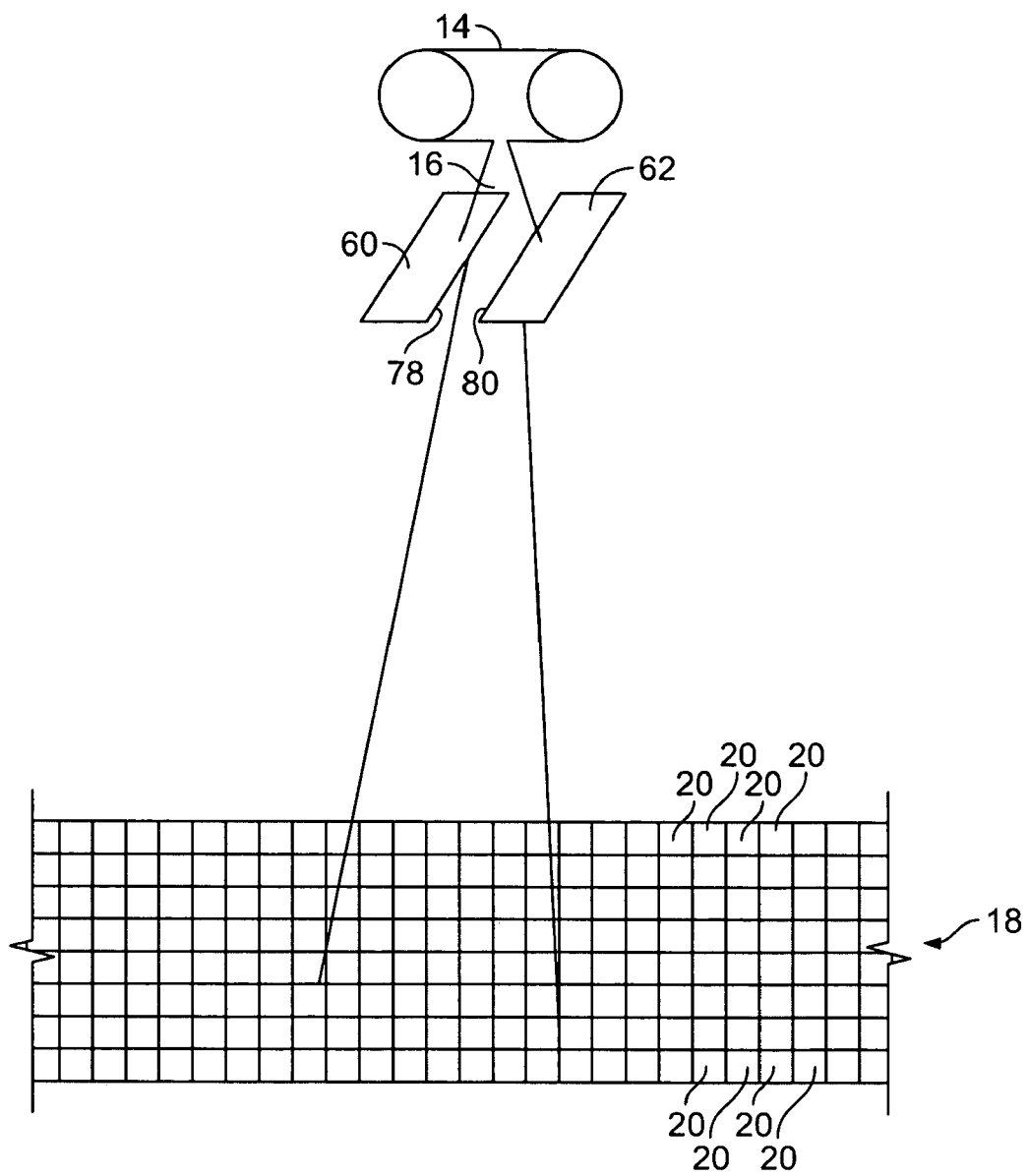
FIG. 3 is a schematic representation of a radiation beam, collimator, and part of a multirow detector.
Figure 4:
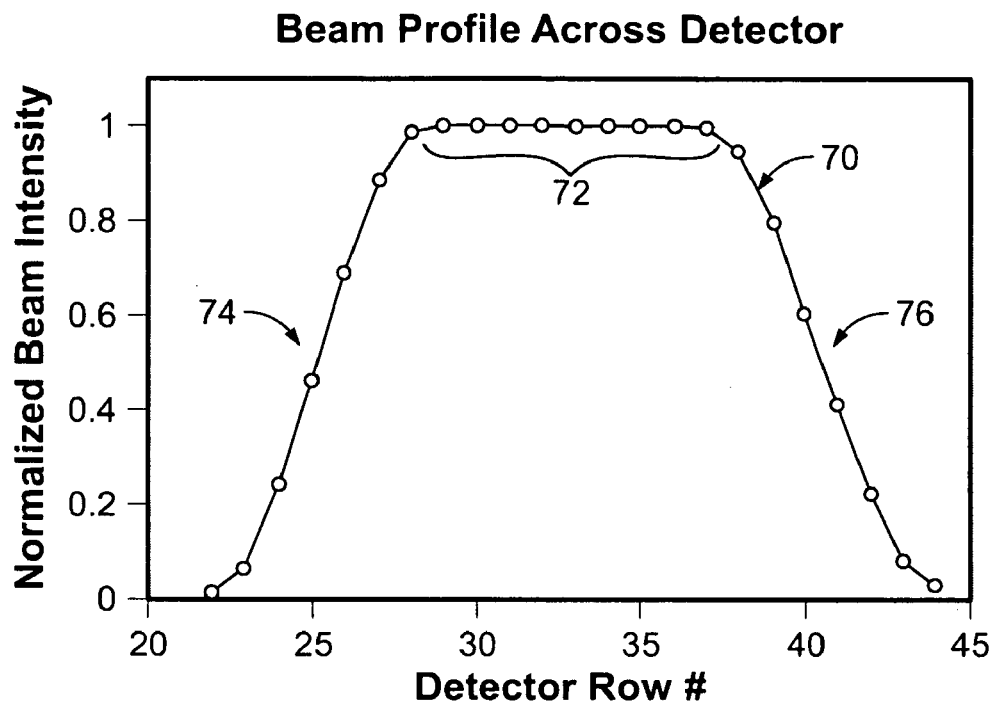
FIG. 4 is a plot of a typical beam profile across several rows of a 64 slice CT detector array, wherein beam intensity is uniform across rows 29 through 36 and begins to decay on either end (rows 22-29 and 36-44).

Referring to FIG. 3, CT systems such as CT system 10 (and many other radiation devices) collimate radiation beam 16 using one or more collimators 60, 62 that each have a well-defined edge 78, 80, respectively. The intensity profile of beam 16 after collimation is used in various configurations of the present invention to determine the X-ray (or other radiation) focal spot intensity profile of beam 16. A typical beam intensity profile 70 (or "focal spot profile) in an axial (i.e., z) direction of a CT system 10 is shown in FIG. 4. In this example, the normalized beam intensity is plotted as a function of CT system 10 detector rows of multi-row detector array 18. The example shown in FIG. 4 has uniform beam intensity across row numbers 29 through 36 and begins to decay on either end between row numbers 22-29 and row numbers 36-44, where the row numbers are assigned sequentially. The uniform region 72 of beam 16 is conventionally known as the beam "umbra," and the decaying regions 74, 76 of beam 16 are known as the "penumbra." The shape of penumbras 74, 76 are determined by the size and shape of the focal spot, and is similar to an "edge spread function" used in measuring frequency response of imaging systems. A line spread function of the focal spot profile can be determined using the derivative of the edge spread function.

The relationship between penumbras 74, 76 and focal spot profile 70 can be shown if each physical edge 78, 80 is modeled as a unit step function. If penumbras 74, 76 are well separated, each penumbra profile can be treated separately. A left side collimator 60 can be modeled as a unit step function $u(z-z_c)$ where $z_c$ is the position of the collimator cam. For z locations less than $z_c$, no radiation is allowed to pass through. For z locations greater than $z_c$, all radiation passes through. A right side collimator 62 can be treated similarly, but with a difference in sign, $u(-(z-z_c))$. If the focal spot intensity distribution 70 is given by $f(z)$, then the penumbra profiles 74, 76 after collimation, $P(z)$, are given by the convolution of the focal spot intensity distribution with the unit step function times a magnification factor, m, $$P(z) = m \cdot f(z) * u(z - z_c) =$$
$$m \cdot \int f(z')u(z - z_c - z')dz' = m \cdot \int_{-\infty}^{z} f(z' - z_c)dz'$$

Focal spot intensity distribution 60 can be recovered using a function of the penumbra profile 74 on the left side, for example, the derivative of the penumbra profile 74 on the left side, $f(z)=P'(z+z_c)/m$.

On right side penumbra 76, the relationship is similar but with an extra negative sign, $f(z)=-P'(z+z_c)/m$.

The magnification factor, m, is given by $m=D_{cd}/D_{fc}$, where $D_{cd}$ is the distance from collimators 60, 62 to the detector, and $D_{fc}$ is the distance from the focal spot to collimators 60, 62.

Figure 5:
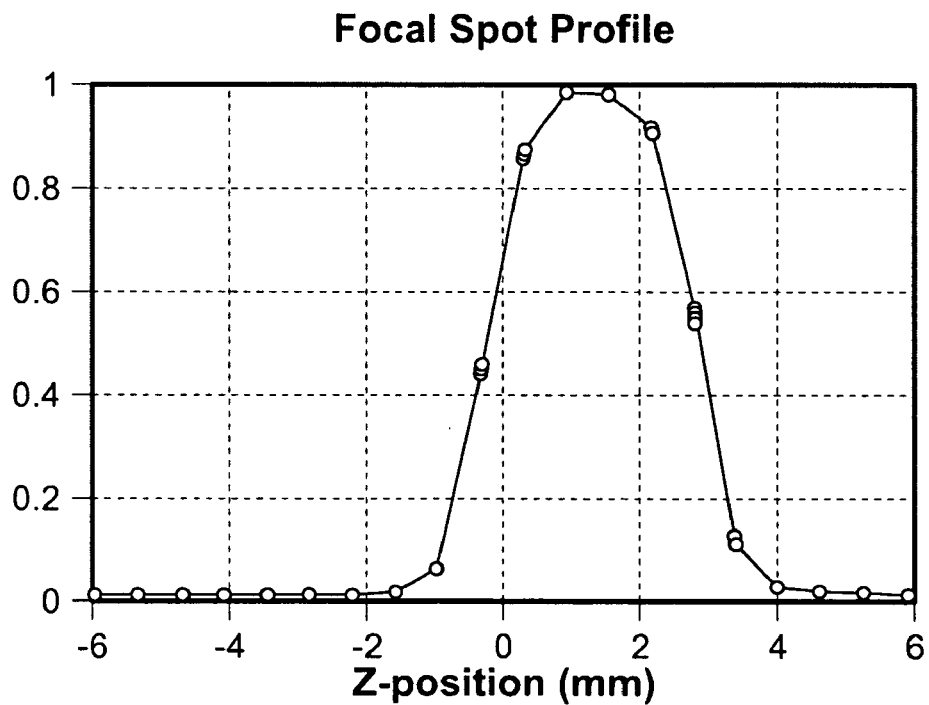
FIG. 5 is a plot of a focal spot profile obtained by taking a derivative of a beam profile, wherein twenty profiles are plotted using data from the center 20 elements of each detector row, showing the reproducibility of the calculation on a CT imaging system.

The derivative of the penumbra profile, $-P'(z)$, is plotted in FIG. 5. On the x-axis, the size of the detector rows (0.625 mm) has been used to translate the axis from detector row numbers used in FIG. 3 into units of distance (mm). Zero is defined to be the center of detector array 18 (between rows 32 and 33 of this 64 slice detector). Because there are many columns (channels) in each detector row of CT detector 10 in some configurations, many profiles can be plotted. In FIG. 5, 20 profiles are plotted showing the reproducibility of the calculation on a configuration of CT imaging system 10.

Although the penumbra intensity profiles 74, 76 are measured in this example using discretely spaced detector 18 rows, penumbra intensity profiles 74, 76 can also be measured using a single detector 18 row and moving collimator 60, 62 edges. Also, penumbra intensity profiles 74, 76 can be measured using a single detector 18 row and constant collimator 60, 62 edges, but translating focal spot intensity profile 70. Finally, it should be clear that although in this example the focal spot profile 70 in the 'z' direction is measured (length), the method is equally applicable to measuring the focal spot 'width' ('x' direction) if a sharp edge is available. More generally, the focal spot shape can be determined.

Figure 6:
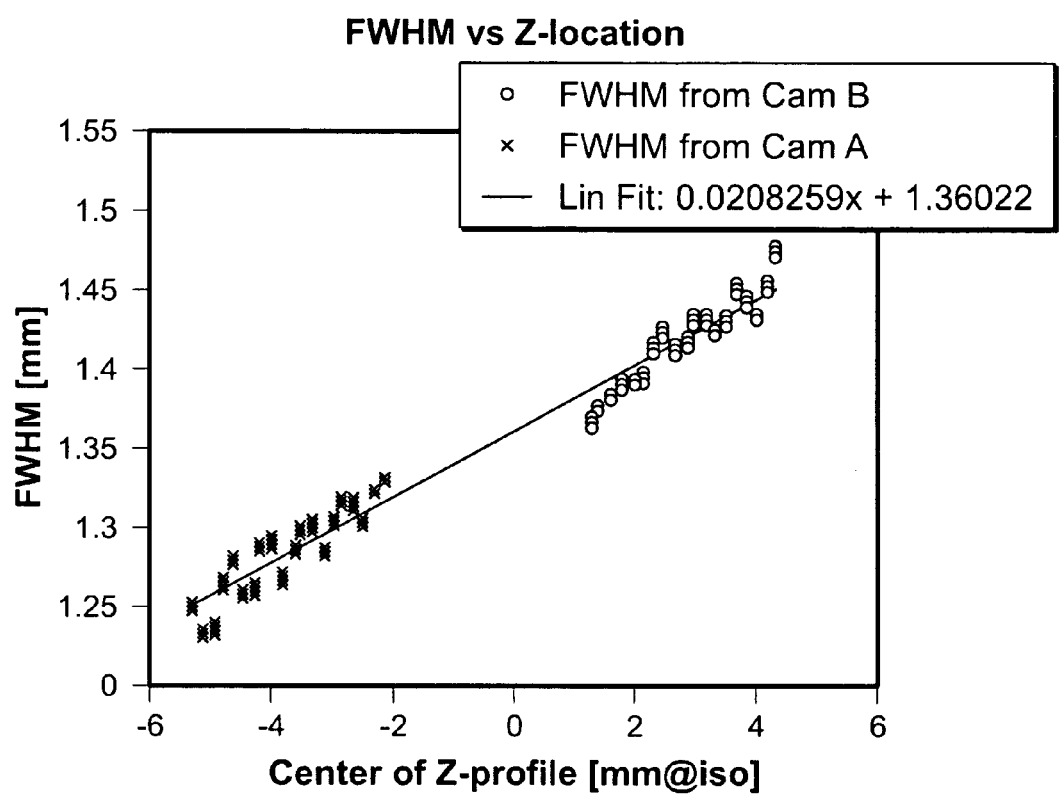
FIG. 6 is a plot of full width at half maximum of a focal spot profile as a function of the z-position of the center of the profile wherein the apparent focal spot size changes depending on the position of the profile on the detector. These changes are result from the geometry of the X-ray tube used in the example, wherein the focal spot is projected from an anode surface that is at a slight angle (e.g. 7 degrees) from the axial plane.

In FIG. 5, the focal spot profile was centered at approximately 1 mm from the center of detector array 18. If collimator edge 78 is positioned at a different 'z' location, beam penumbra 74 on detector array 18 will shift accordingly and the profile will also be centered at a new 'z' location. The "effective" focal spot profile 70 can thus be measured as a function of the position on detector array 18. The full width at half maximum of focal spot profile 70 is plotted in FIG. 6 as a function of the z-position of the center of the profile. The effective focal spot size and shape vary depending on the position of the profile on detector array 18 due to the geometry of X-ray source 14, since the focal spot is projected from an anode surface that is at a slight angle (e.g. 7 degrees) from the axial plane. The nominal focal spot size quoted by manufacturers is measured at the center location (z=0), and in this example the nominal focal spot size is found from the linear fit shown in FIG. 6 to be 1.36 mm.

Figure 7:
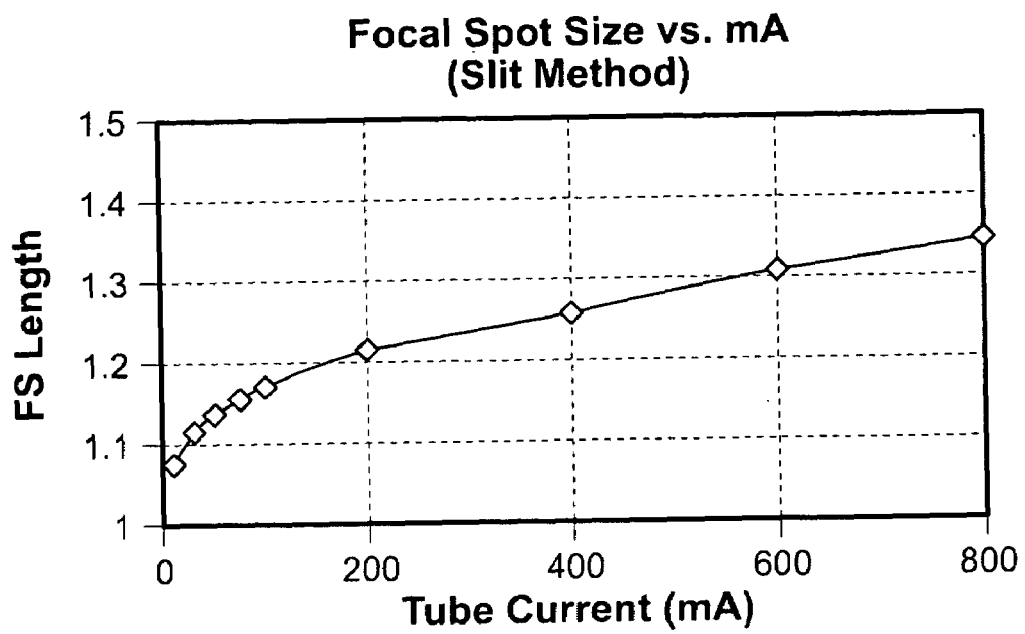
FIGS. 7 and 8 are a comparison of the conventional slit method of measuring focal spot length as a function of tube current (FIG. 7) and with measurements obtained using a configuration of edge method described herein (FIG. 8). The edge method configuration of the present invention accurately portrays the change in focal spot size as a function of tube current.
Figure 8:
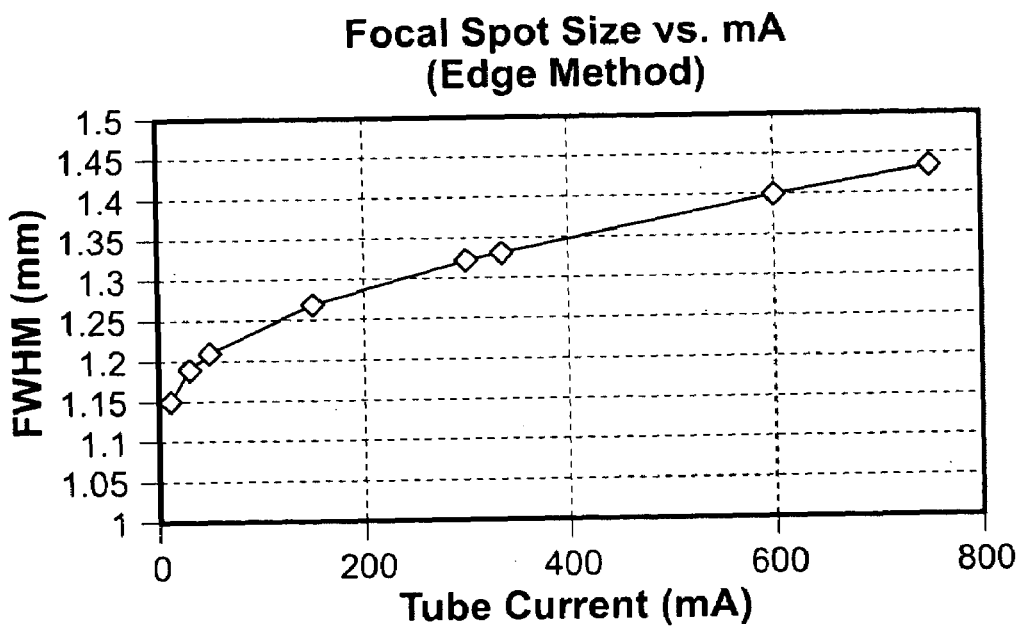

Results of measuring the focal spot size are compared to results obtained using a conventional slit measurement are shown in FIGS. 7 and 8. In particular, the nominal (z=0) focal spot size is shown as a function of the tube current. The edge method configuration of the present invention described above and the slit method yield similar results for the focal spot size as a function of tube current, and the edge method configuration accurately portrays the change in focal spot size as a function of tube current.

Thus, some configurations of the present invention provide a method for measuring focal spot size and/or shape of a radiation beam 16 from a radiation source 18. The method includes collimating the radiation beam using a collimator 60 having a well-defined edge 78. The collimator may be, for example, a cam collimator having a "left" 78 and a "right" 80 edge, as configurations of the present invention are not limited to a single collimator or a single edge. The method further includes measuring an intensity profile 70 of the collimated radiation beam, determining a function such as the derivative of the measured intensity profile, and identifying a metric of the focal spot size using the determined derivative of the measured intensity profile. The metric could be, for example, the number of detector array 18 rows covered by beam 16, a diameter of the focal spot, the shape of the focal spot, or some other quantitative metric. In some configurations, the radiation beam is an x-ray beam.

The source of the x-ray beam can be an x-ray tube 14, and the method can further include emitting the x-ray beam from the x-ray tube in a computed tomographic imaging system 10. The determined metric can be used as a diagnostic for potential failure of the x-ray tube. For example, a change in focal spot size may indicate aging of the x-ray tube. In some configurations, the method includes using the determined metric as feedback for controlling the focal spot size dynamically (using, for example, computer 36 and x-ray controller 28) to improve image quality of the computed tomographic imaging system.

In some configurations, computed tomographic imaging system 10 defines a z-direction, to measure an intensity profile 70 of collimated radiation beam 16, the method further includes measuring a penumbra intensity profile 74 in the z-direction using a plurality of detector 18 rows. In some configurations, measuring an intensity profile of the collimated radiation beam further comprises measuring a penumbra intensity profile in the x-direction.

In some configurations, the moving of edge 78 of collimator 60 and the measuring of an intensity profile 70 of the collimated radiation beam further includes utilizing a single detector 18 row to measure the intensity profile. In some other configurations, collimator edge 78 is not moved relative to radiation source 14, and the measuring of an intensity profile of the collimated radiation beam further includes translating the focal spot intensity profile and utilizing a single detector row to measure the translated intensity profile.

In some configurations of the present invention, an apparatus 10 for measuring focal spot size of a radiation beam 16 is provided. The apparatus includes a detector array 18 sensitive to radiation, a radiation source 14 configured to project a radiation beam 16 at the detector array, a collimator 60 having a well-defined edge 78 and configured to collimate the radiation beam, and a processor (36 or 34, for example) configured to numerically determine derivatives. There can be more than one collimator as well as more than one well-defined edge. The apparatus is configured to measure an intensity profile 70 of the collimated radiation beam, determine a derivative of the measured intensity profile, and identify a metric of the focal spot size using the determined derivative of the measured intensity profile. In some configurations of the present invention, the radiation is x-ray radiation. Also, in some configurations of the present invention, the apparatus is included in a computed tomographic imaging system 10.

In some configurations, the computed tomographic imaging system defines a z-direction, and to measure an intensity profile of the collimated radiation beam, the apparatus is further configured to measure a penumbra intensity profile 76 in the z-direction using a plurality of detector 18 rows. Some configurations are configured to measure a penumbra intensity profile in the x-direction, either instead or in addition to the z-direction.

In various configurations, to move edge 78 of collimator 60 and to measure an intensity profile 70 of collimated radiation beam 18, apparatus 10 is further configured to utilize a single detector 18 row to measure the intensity profile. In other configurations, to hold the collimator edge stationary relative to radiation source 14, and to measure an intensity profile of the collimated radiation beam, the apparatus is further configured to translate the focal spot intensity profile and utilize a single detector row to measure the translated intensity profile.

It will be appreciated that using an edge spread function for measuring focal spot size is facilitated by the availability of sharp edges in a CT imaging system X-ray beam path, such as an X-ray collimator or collimators. Other radiation devices such as a conventional X-ray diagnostic or a radiation therapy treatment device have similar well-defined edges in the radiation beam path, and thus also are suitable for various configurations of the present invention.

The ability to determine a metric of a focal spot size quickly and conveniently on a clinical imaging device is advantageously used in some configurations of the present invention as a diagnostic for potential failure of the tube. Also in some configurations, it is advantageously used as a feedback for controlling the focal spot size dynamically to improve image quality.

While the invention has been described in terms of various specific embodiments, those skilled in the art will recognize that the invention can be practiced with modification within the spirit and scope of the claims.

What is claimed is:

1. A method for measuring focal spot shape of a radiation beam from a radiation source, said method comprising:
    collimating the radiation beam using a collimator having a defined edge;
    measuring an intensity profile of the collimated radiation beam;
    determining a function that is a derivative of the measured intensity profile; and
    determining a metric of the focal spot using the determined function of the measured intensity profile.

2. A method in accordance with claim 1 wherein the radiation beam is an x-ray beam.

3. A method in accordance with claim 2 wherein the radiation source is an x-ray tube, and further comprising emitting the x-ray beam from the x-ray tube in a computed tomographic imaging system.

4. A method in accordance with claim 3 further comprising using the determined metric as a diagnostic for potential failure of the x-ray tube.

5. A method in accordance with claim 1, further comprising emitting the x-ray beam from the x-ray source in an imaging system, and using the determined metric as feedback for controlling the focal spot size dynamically to improve image quality of the imaging system.

6. A method in accordance with claim 1, further comprising emitting the x-ray beam from the x-ray source in a computed tomography imaging system, wherein the computed tomographic imaging system defines a z-direction, and said measuring an intensity profile of the collimated radiation beam further comprises measuring a penumbra intensity profile in the z-direction using a plurality of detector rows.

7. A method in accordance with claim 1, further comprising emitting the x-ray beam from the x-ray source in a computed tomography imaging system, wherein the computed tomographic imaging system defines an x-direction, and said measuring an intensity profile of the collimated radiation beam further comprises measuring a penumbra intensity profile in the x-direction.

8. A method in accordance with claim 1 wherein said method further comprises moving the edge of the collimator and said measuring an intensity profile of the collimated radiation beam further comprises utilizing a single detector row to measure the intensity profile.

9. A method in accordance with claim 1 wherein said collimator edge is not moved relative to the radiation source, and further wherein said measuring an intensity profile of the collimated radiation beam further comprises translating the focal spot intensity profile, and utilizing a single detector row to measure the translated intensity profile.

10. A method in accordance with claim 1 further comprising using the determined metric as a diagnostic for potential failure of the radiation source.

11. A method in accordance with claim 1, further comprising using the determined metric as feedback for dynamically controlling the focal spot size.

12. A method in accordance with claim 1, wherein said metric comprises at least one of a number of detector array rows covered by a beam, a size of a beam, a diameter of the focal spot, and a shape of the focal spot.

13. An apparatus for measuring focal spot shape of a radiation beam, said apparatus comprising:
   a detector array sensitive to radiation;
   a radiation source configured to project a radiation beam at the detector array;
   a collimator having a defined edge and configured to collimate the radiation beam; and
   a processor configured to numerically determine a function of a measured intensity profile;
   said apparatus configured to:
      measure an intensity profile of the collimated radiation beam;
      determine a function that is a derivative of the measured intensity profile; and
      determine a metric of the focal spot using the determined function of the measured intensity profile.

14. An apparatus in accordance with claim 13 wherein the radiation is x-ray radiation.

15. An apparatus in accordance with claim 14 wherein said apparatus is included in a computed tomographic imaging system.

16. An apparatus in accordance with claim 15 wherein the computed tomographic imaging system defines a z-direction, and to measure an intensity profile of the collimated radiation beam, said apparatus further configured to measure a penumbra intensity profile in the z-direction using a plurality of detector rows.

17. An apparatus in accordance with claim 15 wherein the computed tomographic imaging system defines an x-direction, and to measure an intensity profile of the collimated radiation beam, said apparatus further configured to measure a penumbra intensity profile in the x-direction.

18. An apparatus in accordance with claim 13 further configured to move the edge of the collimator, and wherein to measure an intensity profile of the collimated radiation beam, said apparatus further configured to utilize a single detector row to measure the intensity profile.

19. An apparatus in accordance with claim 13 configured to hold the collimator edge stationary relative to the radiation source, and wherein to measure an intensity profile of the collimated radiation beam, the apparatus is further configured to translate the focal spot intensity profile and utilize a single detector row to measure the translated intensity profile.

* * * * *